United States Patent
Abe

(10) Patent No.: US 9,546,956 B2
(45) Date of Patent: *Jan. 17, 2017

(54) METHOD OF INSPECTING SEMICONDUCTOR LIGHT-EMITTING DEVICE AND METHOD FOR MANUFACTURING SEMICONDUCTOR LIGHT-EMITTING DEVICE

(71) Applicant: NICHIA CORPORATION, Anan-shi (JP)

(72) Inventor: Masatoshi Abe, Anan (JP)

(73) Assignee: NICHIA CORPORATION, Anan-shi (JP)

( * ) Notice: Subject to any disclaimer, the term of this patent is extended or adjusted under 35 U.S.C. 154(b) by 452 days.

This patent is subject to a terminal disclaimer.

(21) Appl. No.: 14/179,423

(22) Filed: Feb. 12, 2014

(65) Prior Publication Data

US 2014/0234994 A1    Aug. 21, 2014

(30) Foreign Application Priority Data

Feb. 18, 2013   (JP) ................................ 2013-029233

(51) Int. Cl.
| | |
|---|---|
| *H01L 21/66* | (2006.01) |
| *G01N 21/64* | (2006.01) |
| *G01N 21/95* | (2006.01) |
| *H01L 33/00* | (2010.01) |

(52) U.S. Cl.
CPC ...... *G01N 21/6489* (2013.01); *G01N 21/9501* (2013.01); *H01L 33/0095* (2013.01)

(58) Field of Classification Search
CPC .................................................... H01L 21/66
See application file for complete search history.

(56) References Cited

U.S. PATENT DOCUMENTS

2009/0136120 A1    5/2009   Onushkin et al.

FOREIGN PATENT DOCUMENTS

| | | |
|---|---|---|
| JP | 63-250835 A | 10/1988 |
| JP | 2004-170374 A | 6/2004 |
| JP | 2006-266780 A | 10/2006 |
| JP | 2009-128366 A | 6/2009 |

*Primary Examiner* — Marvin Payen
(74) *Attorney, Agent, or Firm* — Foley & Lardner LLP

(57) ABSTRACT

An inspection method for a semiconductor light-emitting device includes an image capturing step for capturing an image of photoluminescence released from the active layer, an inspection region extracting step for extracting an inspection region from the captured image; a luminance average determination step for, determining the semiconductor light emitting device as defective when a luminance average is smaller than a predetermined threshold, a luminance variance determination step for determining the semiconductor light emitting device as defective when a luminance variance is larger than a predetermined threshold, a color determination step for determining the semiconductor light-emitting device as defective when a pixel in which a color component indicating a photoluminescence intensity of light released from the active layer and having a wavelength shorter than the original emitting wavelength, and a total determination step for totally determining the semiconductor light-emitting device as defective when determined in at least one of these determination results within the inspection region.

19 Claims, 6 Drawing Sheets

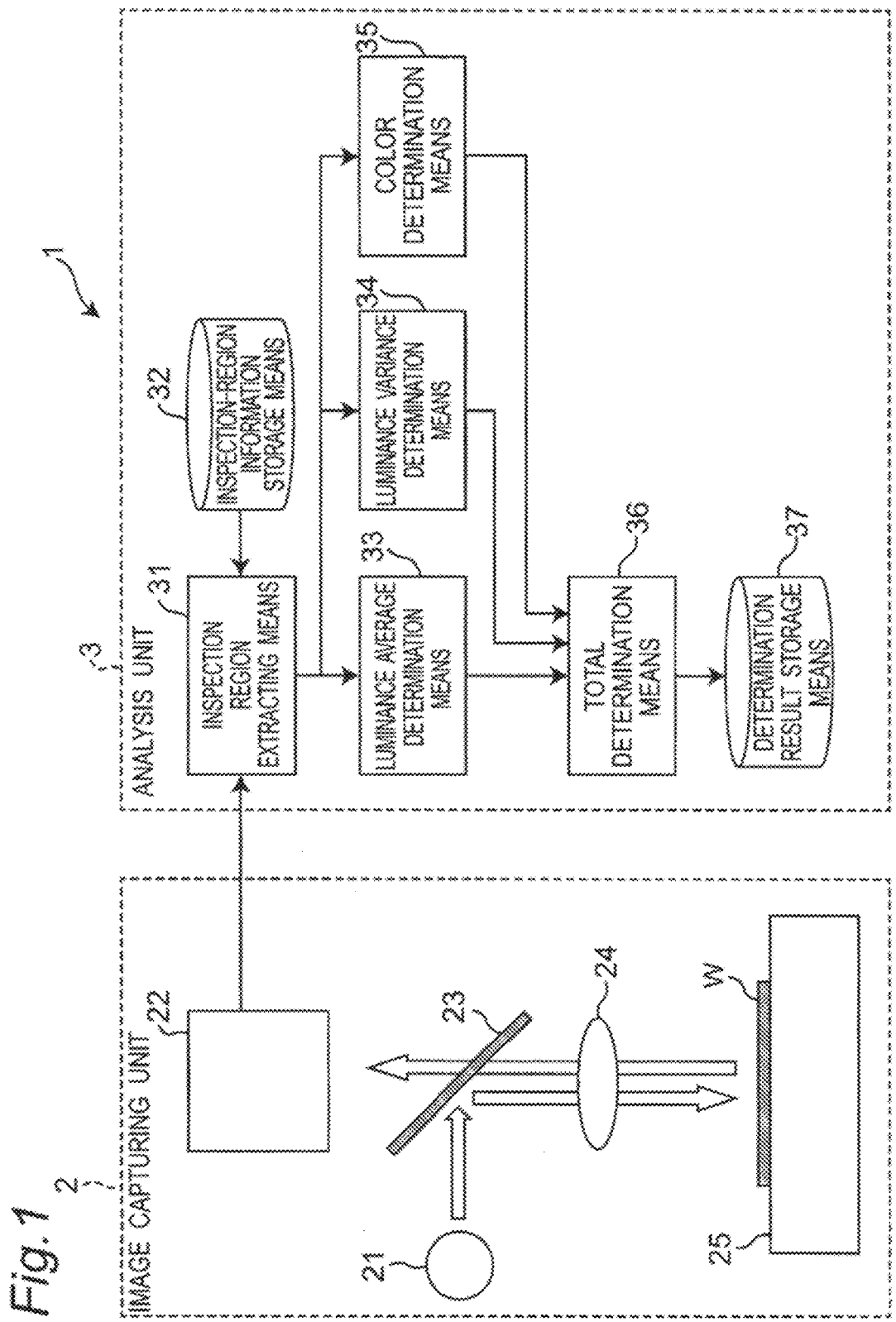

LUMINANCE COMPONENT

R COMPONENT

G COMPONENT

B COMPONENT

INSUFFICIENT LUMINANCE

BLUE LIGHT EMISSION

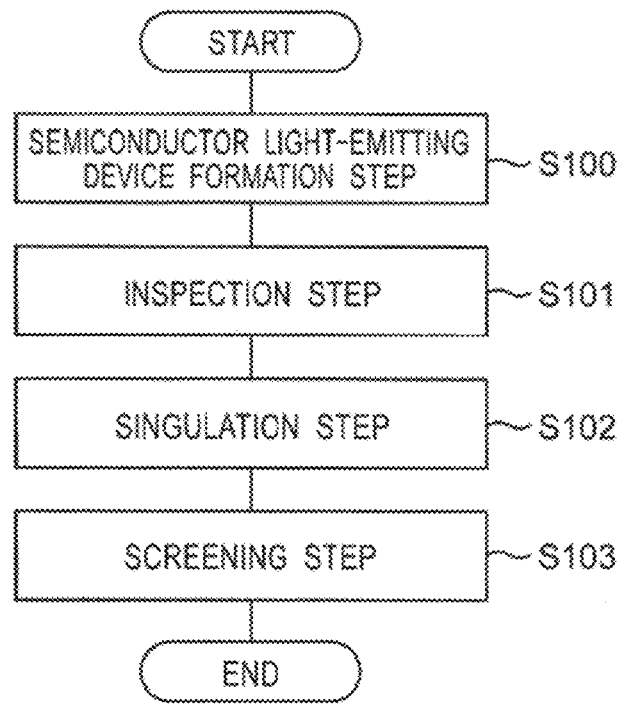

METHOD OF INSPECTING SEMICONDUCTOR LIGHT-EMITTING DEVICE AND METHOD FOR MANUFACTURING SEMICONDUCTOR LIGHT-EMITTING DEVICE

CROSS-REFERENCE TO RELATED APPLICATIONS

This application claims the benefit of Japanese patent application No. 2013-029233, filed on Feb. 18, 2013, which is incorporated by reference.

TECHNICAL FIELD

The present invention relates to an inspection method for a semiconductor light-emitting device and a manufacturing method for a semiconductor light-emitting device including the inspection method.

BACKGROUND ART

Generally, LED (Light-Emitting Diode), which is semiconductor light-emitting device, is manufactured by stacking semiconductor layers of mutually different conductive types on a growth substrate to sandwich an active layer therebetween and further by forming electrodes on the semiconductor layers of the individual conductive types. Manufactured semiconductor light-emitting devices are subjected to inspections for light emitting performance and the like so that acceptable devices are selected.

As inspections for light emitting performance of semiconductor light-emitting devices in their wafer state, there have conventionally been performed appearance inspections for inspecting the presence of flaws or the like under visible light, and light emitting inspections in which light emitting is performed by providing electric currents between positive and negative pad electrodes with use of a prober. In the light emitting inspection with a prober, since the needle (probe) of the prober needs to be put into contact with the electrodes of individual semiconductor light-emitting devices, there have been involved a quite long time for inspections and a fear of flaws on the semiconductor light-emitting devices due to the contact of the probe. Moreover, with small-sized semiconductor light-emitting devices, because their pad electrodes are also small in size, there has been difficulty in properly contacting of the probe with the devices.

Therefore, as a method of inspection for light emitting performance without providing electric currents through the semiconductor light-emitting devices, there has been proposed a method that the active layer of semiconductor light-emitting devices is excited with light irradiation and photoluminescence released from the excited active layer is observed.

For example, Japanese Unexamined Patent Application Publication No. 2009-128366 describes a light-emitting device inspection method including the steps of irradiating a semiconductor light-emitting device with ultraviolet light, capturing a light emitting image generated by photoluminescence effects in the active layer and the n-type semiconductor layer with use of a CCD (Charge Coupled Device) camera and, based on the hue or photoluminescence intensity information therefrom, determining quality of the semiconductor light-emitting device. In this inspection method, the quality is determined by taking advantage of the fact that when the emitting amount of blue light obtained by the photoluminescence effect from the active layer is small due to manufacturing defects or the like, the hue of emitted light observed as a color mixture with yellow light obtained by the photoluminescence effect from the n-type semiconductor layer differs from that of acceptable devices or the photoluminescence intensity as a whole is lower than that of acceptable devices.

CITATION LIST

Patent Literature

Patent literature 1: Japanese Unexamined Patent Application Publication No. 2009-128366

SUMMARY OF INVENTION

As described above, the inspection method described in Japanese Unexamined Patent Application Publication No. 2009-128366 is so designed as to determine the quality of light-emitting devices by detecting differences in hue or photoluminescence intensity due to light-emitting defects of the active layer from those of acceptable devices.

Meanwhile, the inventor of the present application has found that in addition to light of an original wavelength, light of wavelength shorter than that may be observed as it is mixed with the light released from the active layer by the photoluminescence effect, with the results that the color tone of the luminescent color differs from that of acceptable devices and that light-emitting devices in which light of shorter wavelength is observed, even if initially having enough photoluminescence intensity, may decline in photoluminescence intensity or cease to emit light due to failure as the device is continued to use. On this occasion, the hue of luminescent color in defective devices targeted as an inspection object of the inspection method of the invention is different from the hue of photoluminescent color in defective devices targeted as an inspection object of the inspection method described in Japanese Unexamined Patent Application Publication No. 2009-128366. For this reason, with the inspection method described in Japanese Unexamined Patent Application Publication No. 2009-128366, it has been the case that light-emitting devices emitting light in which short-wavelength light is mixed cannot be detected properly as defective devices.

The present invention, having been accomplished in view of these and other problems, has an object of providing inspection methods for a semiconductor light-emitting device, as well as a semiconductor light-emitting device manufacturing method including this inspection method as a process, for properly detecting defective devices through analyzing images of photoluminescence released from semiconductor light-emitting devices excited by light irradiation.

In order to solve the above-described problems, an inspection method for a semiconductor light-emitting device having an active layer emitted light of a predetermined first wavelength, comprising: an image input step for irradiating light of a wavelength shorter than the first wavelength to the semiconductor light-emitting device, capturing image of photoluminescence emitted from the active layer and inputting the captured image; an inspection region extracting step for extracting a region of the semiconductor light-emitting device based on the captured image, as an inspection region; and a color determination step for determining the semiconductor light-emitting device as defective when a pixel having a pixel value of a color component indicating a photoluminescence intensity of a second wavelength light of a shorter wavelength than the first wavelength is larger than a predetermined first threshold is present within the inspection region.

Also, a manufacturing method for a semiconductor light-emitting device according to the invention comprises: a semiconductor light-emitting device formation step for forming a semiconductor light-emitting device; an inspection step for inspecting the semiconductor light-emitting device formed in the semiconductor light-emitting device formation step to determine whether or not the semiconductor light-emitting device is defective; and a screening step for screening the semiconductor light-emitting device as an acceptable device when the semiconductor light-emitting device is not determined as defective in the inspection step, in which the inspection step is carried out according to the inspection method for a semiconductor light-emitting device as described above.

According to the inspection method for a semiconductor light-emitting device of the invention, since a semiconductor light-emitting device that releases photoluminescence having a wavelength shorter than an intrinsic wavelength from the active layer is determined as defective, light-emitting devices that are different in color tone from that of acceptable devices and that may decline in intensity, or fail and cease to emit light as continued to use can properly be detected.

Also, according to the manufacturing method for a semiconductor light-emitting device of the invention, since semiconductor light-emitting devices are screened based on the quality determination results by the above-described inspection method, defective devices can properly be excluded.

BRIEF DESCRIPTION OF DRAWINGS

FIG. 1 is a view showing a configuration of an inspection apparatus for performing an inspection method for a semiconductor light-emitting device according to a first embodiment of the present invention;

FIG. 6 is a flowchart showing the flow of a manufacturing method for a semiconductor light-emitting device according to a second embodiment of the invention.

DESCRIPTION OF EMBODIMENTS

Hereinbelow, inspection methods for a semiconductor light-emitting device and manufacturing methods for a semiconductor light-emitting device according to embodiments of the present invention will be described in detail with reference to the accompanying drawings. It is to be noted here that the accompanying drawings referenced in the following description schematically show the invention so that scales, intervals, positional relations and the like among individual members may be exaggerated or part of those members may be omitted in depiction. Also in the following description, the same designations and reference signs denote the same or equivalent members in principle with their detailed description omitted as appropriate.

First Embodiment

Principle of Inspection Method

Referring first to FIGS. 2A to 2F and FIG. 3, the principle of the inspection method for a semiconductor light-emitting device (hereinafter, referred to as "inspection method" as appropriate) according to a first embodiment of the invention will be described.

Figure 3:
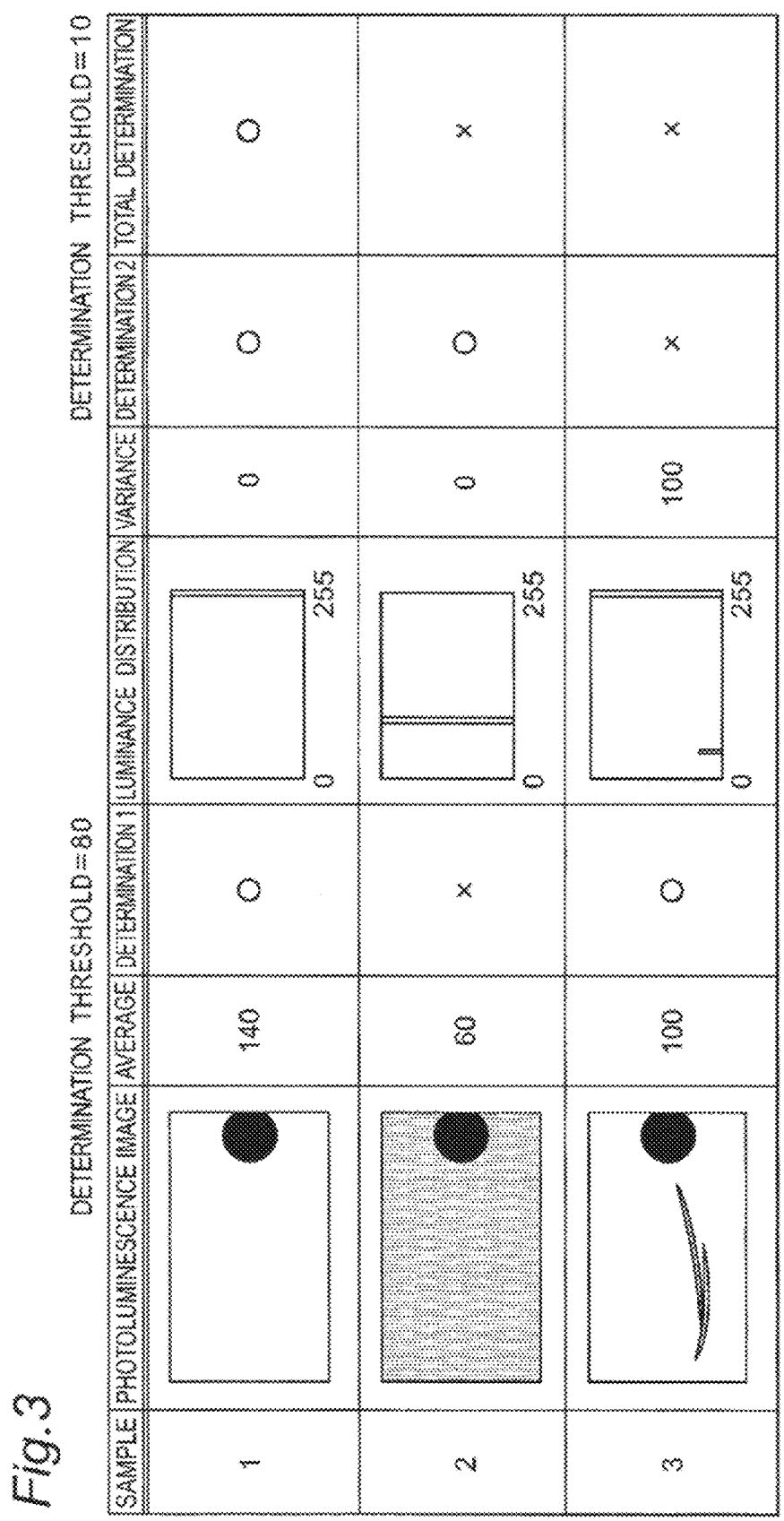
FIG. 3 is an explanatory view for explaining an outline of the inspection method for a semiconductor light-emitting device according to the first embodiment of the invention.

FIG. 3 shows an example in which images of photoluminescence are schematically shown for explanation of the principle of the inspection method.

The inspection method according to the first embodiment of the invention is intended to determine whether or not a semiconductor light-emitting device (hereinafter, referred to as light-emitting device as appropriate), which is an inspection object, is acceptable or defective through the steps of irradiating the light-emitting device with light for excitation of the active layer, and analyzing an image of photoluminescence obtained by capturing an image of photoluminescence released from the excited active layer.

More specifically, with an inspection region where a single-unit light-emitting device is captured, the inspection method according to this embodiment is designed to determine the light-emitting device as defective when the light-emitting device has a pixel in which the pixel value of a color component indicating a photoluminescence intensity of a light of a second wavelength, which is shorter than a first wavelength that is the original wavelength released from the active layer is larger than a predetermined threshold (first threshold).

Also, as a preferred embodiment, the inspection method according to this embodiment further determines the light-emitting device as a defective device when an average of photoluminescence intensity emitted from a light-emitting region, which is an inspection region, is smaller than a predetermined threshold (second threshold), and moreover determines the light-emitting device as a defective device also when a variation of photoluminescence intensity in the inspection region is larger than a predetermined threshold (third threshold). That is, the light-emitting device is determined as a defective device when determined as defective in at least one of the three determination methods.

The three determination methods are explained in further details below.

(Determination Based on Color)

As described before, the inventor of the present application has found that with excitation light applied to a light-emitting device, when light of a second wavelength shorter than a first wavelength that is an original wavelength to be released from the excited active layer is observed, the color tone becomes different from that of acceptable devices. Moreover, the inventor has also found that the light-emitting device may deteriorate with time elapses so as to decline in photoluminescence intensity or fail and cease to emit light due to failure as the device is continued to use.

With excitation light applied, light of a first wavelength is released from the active layer by the photoluminescence effect. In this case, a light-emitting device from which light of a second wavelength is released in addition to the first-wavelength light or instead of the first-wavelength light is determined as a defective device. This second wavelength is shorter than the first wavelength but longer than the wavelength of the excitation light.

In addition, it is considered that the light of the second wavelength is released when the thickness of the active layer is thinner than a predetermined value due to defects occurring during the growth of the semiconductor layer.

For example, in a case of a light-emitting device that emits light of green color as the first-wavelength light, the second-wavelength light is blue light. Also, excitation light may be light of wavelength shorter than the second wavelength, e.g., light of 385-430 nm.

Figure 2A:
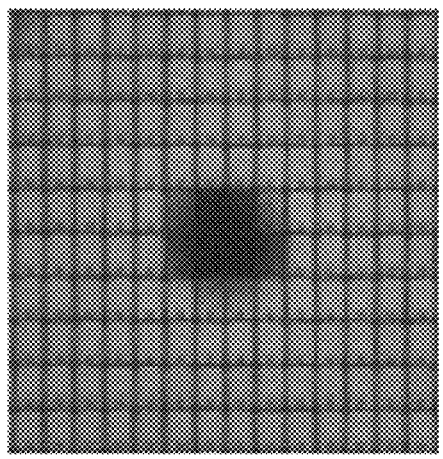
FIG. 2A is an explanatory view for explaining an outline of the inspection method for a semiconductor light-emitting device according to the first embodiment of the invention, where the luminance component of an image of photoluminescence is shown.
Figure 2B:
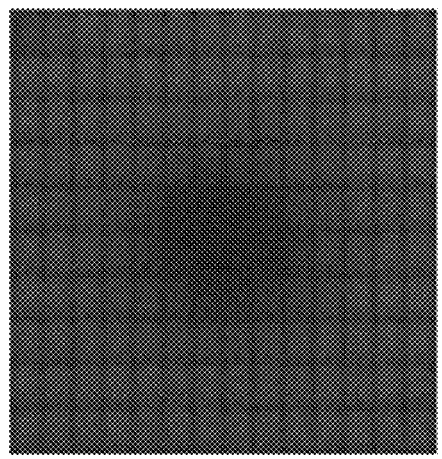
FIG. 2B is an explanatory view for explaining an outline of the semiconductor light-emitting device inspection method according to the first embodiment of the invention, where the R component of the image of photoluminescence is shown.

FIGS. 2A to 2F show an example of images of photoluminescence of light-emitting devices that emit green light as the first wavelength with use of a nitride semiconductor as a semiconductor material. As shown in FIG. 2A, with observation of the luminance component, it can be seen that wafer-state light-emitting devices (14×10 pcs. in this case) formed in two-dimensional array are captured.

It is noted that in the images of individual components shown in FIGS. 2A to 2D, the degree of brightness (whiteness) in depiction increases as degree of the relevant component increases. Further, in each of FIGS. 2A to 2F, longitudinal-and-lateral grid-like dark lines are dividing regions between light-emitting devices, and black circular regions on the lower-edge side in each light-emitting device are regions where the p-type semiconductor layer and the active layer have been eliminated for formation of the n-side electrode, where both regions are non-emitting regions that structurally do not emit light.

Figure 2C:
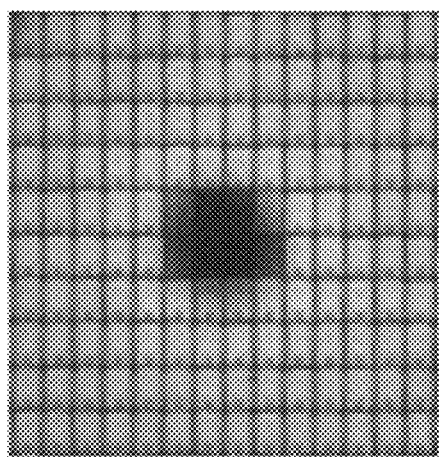
FIG. 2C is an explanatory view for explaining an outline of the inspection method for a semiconductor light-emitting device according to the first embodiment of the invention, where the G component of the image of photoluminescence is shown.
Figure 2D:
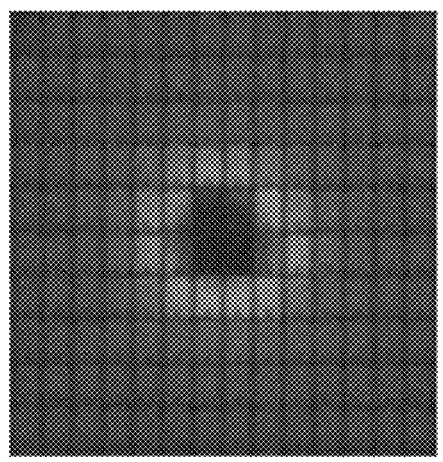
FIG. 2D is an explanatory view for explaining an outline of the inspection method for a semiconductor light-emitting device according to the first embodiment of the invention, where the B component of an image of photoluminescence is shown.

As shown in FIGS. 2A and 2C, with observation of the luminance component or G (green) component, it can be seen that 4×2 pc. light-emitting devices near center of each of FIG. 2A and FIG. 2C (light-emitting devices at hatched positions in FIG. 2E) hardly emit green light. Also, as shown in FIG. 2D, with observation of the B (blue) component, it can be seen that part of 4×2 pc. light-emitting devices near center of the FIG. 2D and their neighboring light-emitting devices (light-emitting devices at hatched positions in FIG. 2F) emit blue light, which is the second-wavelength light. In addition, in this example, as the light-emitting devices emit green light, they hardly release light of wavelength longer than the second wavelength. Accordingly, with respect to the R (red) component, its pixel value is nearly '0' even in light-emitting regions so that such a region is observed dark as a whole.

Figure 2E:
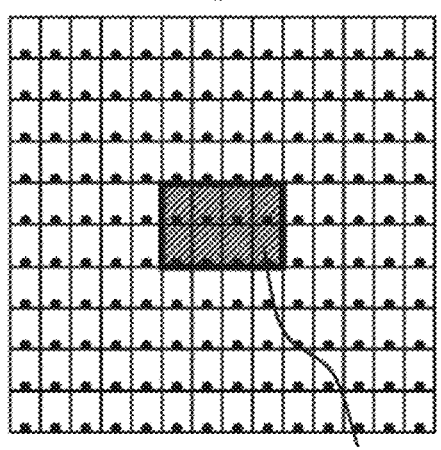
FIG. 2E is an explanatory view for explaining an outline of the inspection method for a semiconductor light-emitting device according to the first embodiment of the invention, where a light-emitting device of insufficient luminance is shown.

The 4×2 pc. light-emitting devices hatched in FIG. 2E, being low photoluminescence intensity of green color, are light-emitting devices determined as defective by a later-described determination method based on the photoluminescence intensity average because those light-emitting devices are low in intensity of green light, which is the light of the first emitting wavelength, and therefore low in luminance.

Figure 2F:
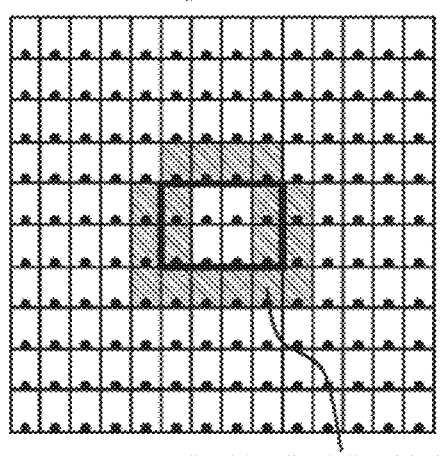
FIG. 2F is an explanatory view for explaining an outline of the inspection method for a semiconductor light-emitting device according to the first embodiment of the invention, where a light-emitting device that emits blue light is shown.

Also, 18 pc. light-emitting devices hatched in FIG. 2F show those devices in which pixels having an intensity of blue light that is the second-wavelength light larger than a predetermined threshold (first threshold) have been detected in inspection regions of their corresponding images of photoluminescence. These light-emitting devices are determined as defective in this determination method.

In addition, the threshold value (first threshold) for the photoluminescence intensity of the second wavelength may be, for example, about $1/10$ of the intensity of the first wavelength in acceptable devices. That is, it is allowable that a light-emitting device is determined as defective on condition that the light-emitting device includes a pixel that emits light of the second wavelength at intensity of about one tenth ($1/10$) intensity of the original photoluminescence intensity.

(Determination Based on Photoluminescence Intensity Average)

It is determined whether or not an intensity of photoluminescence emitted by a light-emitting device is equal to or larger than a specified threshold on a single-unit light-emitting device basis. As described before, the light-emitting devices hatched in FIG. 2E are those determined as defective based on the photoluminescence intensity average.

Referring now to FIG. 3, the method for determining the quality of light-emitting devices by using the photoluminescence intensity average of photoluminescence released from the active layer is explained. Shown in the field of image of photoluminescence in FIG. 3 are images obtained by capturing an aspect that the active layer of the light-emitting device excited by light irradiation releases photoluminescence.

In samples 1-3 shown in FIG. 3, as described above, images of photoluminescence are shown with luminance used as the index indicating the photoluminescence intensity. In this case, it is assumed that each luminance is expressed in 256-step pixel values where the luminance of the darkest portion is '0' and the luminance of the brightest portion is '255.'

In the image of photoluminescence of each sample, a black circular region on the right edge side is a non-emitting region where the p-type semiconductor layer and the active layer are eliminated for formation of the n-type electrode so that the region structurally does not emit light.

The luminance average of a light-emitting region, which is an inspection region of each sample, is as shown in the 'average' field of FIG. 3. In this case, it is assumed that a determination threshold for making a quality determination based on the luminance average is '80'. Also, determination results by this determination method are shown by ◯ (acceptable device) and X (defective device) in the field of 'Determination 1.'

In the case where the entire surface except the non-emitting region emits light with sufficient intensity as in the case of sample 1, the semiconductor light-emitting device is determined as an acceptable device. In the case where the entire surface emits light with insufficient intensity as in sample 2, the semiconductor light-emitting device is determined as a defective device. Sample 3, although partly having a light-emitting defective region due to an internal defect caused during the manufacture, yet emits light at a predetermined intensity or higher as one light-emitting device. Therefore, sample 3 is determined as an acceptable device by the determination based on luminance average.

Light-emitting devices having such light-emitting defective regions as in sample 3 can emit light at a predetermined intensity or higher immediately after they have been manufactured. However, the light-emitting devices are highly likely to decline in intensity, moreover to fail and cease to emit light, due to time deterioration. Therefore, the light-emitting devices should basically be rejected as defective devices.

Such defects causing light-emitting defects as shown above, when externally appearing, can be detected by conventional appearance inspections. However, for example, defects occurring to the internal active layer can hardly be detected by appearance inspections.

(Determination Based on Luminance Variance)

The third determination method is designed to detect the presence of any light-emitting defective region formed in the light-emitting region as in sample 3 described above, and to determine the light emitting device is a defective device when a light-emitting defective region is detected. The detection of a light-emitting defective region is performed based on the index indicating variation of photoluminescence intensity (e.g., variance or standard deviation) in the light-emitting region. That is, the presence of any light-emitting defective region is determined by utilizing the property that the variation of photoluminescence intensity within the light-emitting device increases in the case where a light emitting defective region of very low photoluminescence intensity exists.

Referring to FIG. 3, this determination method is explained in continuation. In FIG. 3, histograms indicating pixel luminance distributions of pixels of the light-emitting regions in samples 1-3 are shown in a field of 'luminance distribution.' These histograms schematically indicate relative frequencies against the frequency of the most frequent luminance on the assumption that the horizontal axis represents the luminance and the vertical axis represents the frequency.

Sample 1 shows that all the pixels emit light at the highest luminance. Therefore, there are no luminance differences among pixels, where the variance, which is the index of variation in photoluminescence intensity, is '0.'

In sample 2, although the luminance is low, yet there are no luminance differences among pixels, where the variance is '0.'

In sample 3, the light-emitting regions include light-emitting defective regions that do not emit light at all or that are considerably lower in luminance level than the other light-emitting regions, where the luminance distributions are bipolarized into the highest luminance and the lowest luminance. Thus, the variance is as large as '100.'

In this case, given that the determination threshold based on the luminance variance is '10,' samples 1, 2 are determined as acceptable devices and sample 3 is determined as a defective device, as marked by ○ (acceptable device) and X (defective device) in the field of 'Determination 2.'

In the case described above, the terms "light-emitting defective regions that are considerably lower in luminance level than the other light-emitting regions" refer to being of lower level than the range of luminance unevenness permitted as acceptable. Also, the examples of the determination threshold by luminance average, the determination threshold by luminance variance, luminance distribution and the like shown in FIG. 3 are schematic exemplifications for explaining the principle of the inspection method and these are not limited. These determination thresholds may appropriately be predetermined by empirically determining distributions of luminance averages and luminance variances in acceptable-device samples as well as distributions of luminance averages and luminance variances in defective device samples so that acceptable devices and defective devices can properly be determined.

In this embodiment, the quality determination based on the luminance average is made by using only the lower-limit threshold, but the determination using the upper-limit threshold may be further performed. Among light-emitting devices having flaws or other defects, in spite of their being defective devices, there are some cases where photoluminescence is observed apparently at luminances higher than those of acceptable light-emitting devices because photoluminescence propagating from adjacent light-emitting devices is diffracted or scattered in the light-extraction plane direction by the defective portions. In the case of such defective light-emitting devices, the quality determination can properly be achieved by setting an upper-limit threshold and determining the light-emitting device as defective also when the luminance average is larger than the upper-limit threshold.

In the case where the upper-limit threshold is provided, gain of an image capturing means 22 is adjusted so that the pixel value corresponding to the highest luminance observed in acceptable light-emitting devices becomes lower than the highest value of the pixel values of an image capturing means 22. With the pixel value given by 8-bit data, the pixel value corresponding to the highest luminance of acceptable light-emitting devices is set to '150' as an example. Then, with the upper-limit threshold set to '150,' light-emitting devices having a luminance average over '150,' i.e. exceeding the highest value of luminance average of acceptable light-emitting devices may appropriately be determined as defective.

(Total Determination)

In the inspection method according to this embodiment, the determination of the quality is made by considering all of a determination result based on the presence of any pixel of released light of the second wavelength at an intensity larger than a predetermined threshold, a determination result based on the luminance average, and a determination result based on the luminance variance. That is, on condition that a light-emitting device is determined as defective in at least any one of those determinations, the light-emitting device is determined as a defective device. In other words, on condition that a light-emitting device is determined as defective in none of the three determinations (i.e. determined as acceptable in all of the three determinations), the light-emitting device is determined as an acceptable device.

In addition, for evaluation of the variance, pixels that structurally become non-emitting regions are excluded. Those pixels that become non-emitting regions, normally having a luminance of '0' or a very low value, indicate a pixel value equivalent to those of light-emitting defective regions due to defects or the like. For this reason, including pixels of non-emitting regions to calculate a variance would make it impossible distinguish the calculated variance from variances resulting when light-emitting defective regions are included.

Thus, in the inspection method of the invention, variances are calculated excluding pixels that structurally become non-emitting regions beforehand. In addition, when no non-emitting regions are involved structurally, pixel values of the entire region of the light-emitting device may be used to calculate the variance.

Also, for calculation of the luminance average, even without excluding pixels of non-emitting regions, lessening the determination threshold in consideration of decreases in the luminance average due to non-emitting regions makes it possible to determine the quality of light emitting device on the same basis as in the case where the non-emitting regions are excluded. However, it is preferable that also for the determinations based on the luminance average, the luminance average is calculated with pixels of non-emitting regions excluded, in which case the luminance average value is increased so that the determination precision is improved.

Also, in the detection of pixels that release light of the second wavelength, there is no need for excluding pixels of non-emitting regions from the inspection regions. This is because none of such pixels are detected as those which release light of the second wavelength and such pixels do not affect determination results. However, as pixels of non-emitting regions are regions that do not need to be inspected and therefore excluding such pixels previously from the inspection regions allows computation quantities for the inspection to be reduced.

Although the quality determination is made by using determination results by the three determination methods in this embodiment, this is not limited. It is appropriate to make a quality determination by using at least a determination result based on color. It is also allowable that the quality total determination may be performed by combination of a determination result based on color and any one of a determination result based on luminance average and a determination result based on luminance variance. Further, given that the determination method is one based on images of photoluminescence as in this embodiment, since the determination based on color and the determination based on luminance (a determination based on luminance average and/or a determination based on luminance variance) can be performed based on common data, the inspection time can be shortened. Moreover, combinations with other determination methods such as an appearance inspection under visible light are also adoptable.

(Configuration of Inspection Apparatus)

Next, the configuration of an inspection apparatus for performing the inspection method according to the first embodiment of the invention will be described with reference to FIG. 1.

As shown in FIG. 1, the inspection apparatus 1 of this embodiment is composed of an image capturing unit 2 and an analysis unit 3.

In this embodiment, a color separation into three colors of R(Red), G(Green), B(Blue) is performed after the inspection region extracting step, but it is not limited. For example, the color separation can be performed before the inspection region extracting step.

The image capturing unit (image input means) 2 is to capture an image of photoluminescence released from the active layer by irradiation of light-emitting devices with excitation light. For this purpose, the image capturing unit 2 in this embodiment includes an irradiating light source 21, an image capturing means 22, a dichroic mirror 23, an objective lens 24, and a mount 25.

In this embodiment, an inspection object W is assumed as a wafer-state one in which light-emitting devices are formed in two-dimensional array in the following description, but this is not limited. For example, the inspection object W may be a single light-emitting device or may be light-emitting devices divided into chips from a wafer division and re-arrayed on a support substrate or the like. Furthermore, the inspection object W may be light-emitting devices obtained by bonding a support substrate on the opposite side surface to a growth substrate of wafer-state light-emitting devices and further peeling the growth substrate off so that the light-emitting devices are transferred to the support substrate.

The irradiating light source 21 is a light source for generating light of wavelength that can excite the active layer of the light-emitting device constituting the inspection object W. The excitation light needs only to include light of shorter wavelength than wavelength of the light emitted from the active layer of the light-emitting device to be inspected. For example, for light-emitting devices that emit green light, blue or purple light can be used as the excitation light. For light-emitting devices that emit blue light, visible light of shorter wavelength than the blue light can be used as the excitation light.

As such an irradiating light source 21 is LED, laser diode, xenon arc lamp, mercury arc lamp, and the like can be used.

In the case where light by the photoluminescence effect is released from semiconductor layers other than the active layer, it is preferable that light of wavelength which are capable of exciting the active layer and which do not excite semiconductor layers other than the active layer is used as the excitation light.

For example, when a GaN (gallium nitride)-based nitride semiconductor is used as the semiconductor material, irradiation of light having a wavelength of 365 nm or lower allows light to be released from not only the active layer but also the n-type semiconductor layer by the photoluminescence effect. Meanwhile, when green light is released from the active layer as light of the first wavelength, for example, light of wavelength of about 385-430 nm can be used as the excitation light. Accordingly, using light of such wavelength as the excitation light makes it possible to selectively excite only the active layer. Thus, inspections of light-emitting devices by each of the determination methods can be performed without influence of light by the photoluminescence effect derived from the semiconductor layers other than the active layer.

Further, in a case where the light source itself has a wide emitting-wavelength range, it is allowable that the irradiating light source 21 is made up by combining together an optical filter and a spectroscope as required so that excitation light for selectively exciting the active layer is generated.

The image capturing means 22 is an image capturing device such as a CCD image sensor and a CMOS (Complementary Metal Oxide Semiconductor) image sensor to capture images of photoluminescence of the inspection object W. The image capturing means 22 outputs data of captured images of photoluminescence to the analysis unit.

The image capturing means 22 can be employed to a color image sensor. With this arrangement, captured images of photoluminescence can be obtained and can be separated into three colors of R (Red), G (Green) and B (Blue), as an example.

In addition, the color components for color separation are not limited to the three colors of R, G, B and may be determined as appropriate depending on the first wavelength and the second wavelength of light-emitting devices to be inspected. In this case, the color separation is preferably performed so as to include a color component having selective sensitivity to the first wavelength and a color component having selective sensitivity to the second wavelength. For example, given a color separation into three color component of the R, G, B and given that the first wavelength is green color and the second wavelength is blue color, the determination based on luminance average and the determination based on luminance variance can be fulfilled by using luminance components calculated by weighting to the individual color components of R, G and B in accordance with relative luminous efficiency or the G component having the highest sensitivity to the first wavelength. The determination based on color can be fulfilled by using the B component having sensitivity to the second wavelength and moreover having low sensitivity to the first wavelength.

Also, for example, in the case where the first wavelength is blue color and the second wavelength is purple color, the image capturing means 22 may be given by using an image capturing means capable of color separation into a color component of blue wavelength range (B component) and a color component of purple wavelength range (purple component). In this case, the determination based on luminance average and the determination based on luminance variance can be performed by using the B component having the highest sensitivity to the first wavelength, and the determination based on color can be performed by using the purple component having sensitivity to the second wavelength and moreover having low sensitivity to the first wavelength.

Also, the color components for color separation are not limited to three or two colors. The color can be separated finely to four or more color components so that color components for use in the individual determination methods are extracted appropriately in correspondence to the first wavelength and the second wavelength of light-emitting devices to be inspected.

The dichroic mirror 23, which is a reflection member having wavelength selectivity of reflected light, reflects light of a particular wavelength range derived from the irradiating light source 21 as excitation light toward the inspection object W side and moreover transmits photoluminescence derived from the inspection object W toward the image capturing means 22 side.

In addition, the dichroic mirror 23 can have such characteristics as to reflect excitation light of desired wavelength according to the inspection object W.

In a case where the light from the irradiating light source 21 is only that of wavelength effective as excitation light, a half mirror can also be used instead of the dichroic mirror 23.

The objective lens 24 is a lens for converging excitation light coming from the irradiating light source 21 via the dichroic mirror 23 to an image capturing region of the inspection object W and for forming an image of photoluminescence derived from the inspection object W on an image capturing surface of the image capturing means 22.

In this embodiment, the dichroic mirror 23 is provided between the image capturing means 22 and the objective lens 24, but without being limited to this, a camera in which an image capturing device and an objective lens are integrally included may also be used.

The mount 25 is for placing and holding thereon the inspection object W. In this embodiment, the mount 25 is formed by using an XY stage which is movable in two directions on a horizontal plane. By driving the XY stage to move the inspection object W within the horizontal plane, an image capturing range of one-time capture by the image capturing means 22 can be changed as required. Thus, images of the inspection object W can be captured in a plurality of divided regions.

The analysis unit 3 is for analyzing an image of photoluminescence of the inspection object W inputted from the image capturing unit 2 to determine the quality of individual light-emitting devices constituting the inspection object W is acceptable or not. For this purpose, the analysis unit 3 in this embodiment includes an inspection region extracting means 31, an inspection-region information storage means 32, a luminance average determination means 33, a luminance variance determination means 34, a color determination means 35, a total determination means 36, and a determination result storage means 37.

The inspection region extracting means 31 receives an input of an image of photoluminescence of the inspection object W from the image capturing means 22 of the image capturing unit 2, then divides the image of photoluminescence into image regions on the light-emitting device basis. Further, with respect to each of the divided image regions on the one light-emitting device basis, extracts only image data of inspection regions as inspection region images, one after another, by referencing inspection-region information which is information for discriminating between inspection regions being inspection objects and non-inspection regions being excluded out of inspection objects in the relevant light-emitting device previously stored in the inspection-region information storage means 32. The inspection region extracting means 31 outputs extracted inspection region images on the light-emitting device basis to the luminance average determination means 33, the luminance variance determination means 34 and the color determination means 35.

Details of the inspection region and the non-inspection region in a light-emitting device will be described later.

The inspection-region information storage means 32 stores inspection-region information that is information for discriminating between inspection regions, which are taken as objects of the inspection, and non-inspection regions, which are not taken as objects of the inspection, in the light-emitting device which is to be inspected. Herein, the terms 'inspection region' refers to a region (light-emitting region) of a light emitting device which includes an active layer and releases photoluminescence due to structural reasons of the light-emitting device is in a plan view (in the plane to be captured) of the light-emitting device. Also, the term 'non-inspection region' refers to a region where no light is emitted due to structural reasons of the light emitting device (non-emitting region) for example, having no active layer so that an n-side electrode is formed. Inspection-region information stored in the inspection-region information storage means 32 is referenced by the inspection region extracting means 31.

In this case, it is assumed that the inspection-region information is previously stored (registered) in the inspection-region information storage means 32 prior to the inspection. Instead of being previously registered as in this embodiment, the inspection-region information may also be inputted to the inspection region extracting means 31, as required, from external, e.g. via communication lines, depending on the type of inspection objects.

The luminance average determination means (photoluminescence-intensity average determination means) 33 receives inputs of inspection region images from the inspection region extracting means 31 on the light-emitting device basis to calculate a luminance average, which is an average of luminance values (photoluminescence intensity) among inspection region images on the light-emitting device basis. Then, the luminance average determination means 33 compares a luminance average threshold (second threshold), which is a predetermined determination threshold, and a calculated luminance average with each other so as to determine the relevant light-emitting device as a defective device when the luminance average is smaller than the luminance average threshold and to determine the light-emitting device as acceptable when the luminance average is equal to or larger than the luminance average threshold. The luminance average determination means 33 outputs a determination result to the total determination means 36.

In this embodiment, the luminance value is used to indicate the degree of the photoluminescence intensity, but it is not limited thereto and other degree may also be used if they indicate the photoluminescence intensity. For example, the index may be the luminance value corresponding to the Y value in the CIE (Commission Internationale de l'Eclairage) 1931 standard colorimetric system, or may be the value calculated by weighting RGB-separated color image data with proper weighting (e.g., 0.3:0.6:0.1) applied to R, G and B in accordance with the relative luminous sensitivity. Still also, the index may be the pixel value for any one of the color components having the highest sensitivity to photoluminescence of the first wavelength, which is photoluminescence from the active layer of an acceptable light-emitting device.

The luminance variance determination means (photoluminescence-intensity variation determination means) 34 receives inputs of inspection region images from the inspection region extracting means 31 on the light-emitting device basis and calculates a luminance variance that is a variance (variation) of luminance values (photoluminescence intensity) in inspection region images on the light-emitting device basis. Then, the luminance variance determination means 34 compares a luminance variance threshold (third threshold), which is a predetermined determination threshold, and a luminance variance with each other so as to determine the relevant light-emitting device as defective when the luminance variance is larger than the luminance variance threshold and to determine the light-emitting device as acceptable when the luminance variance is equal to or smaller than the luminance variance threshold. The luminance variance determination means 34 outputs the determination result to the total determination means 36.

In this embodiment, the luminance variance is used to indicate the degree of a variation of the photoluminescence intensity, but this is not limited thereto. As to photoluminescence intensity, other indices which indicate photoluminescence intensity may also be used as in the foregoing case of the luminance average determination means 33. Also as a degree of the variation, the standard deviation shown Equation (2) or the average deviation shown in Equation (3) can be used instead of the variance shown in Equation (1), and moreover the coefficient of variation (CV) obtained by dividing the standard deviation by the average as shown in Equation (4) can be used.

$$\text{variance} = \Sigma(Xi - Xave)^2/N \quad \text{Eq. (1)}$$

$$\text{standard deviation} = \sqrt{(\text{variance})} \quad \text{Eq. (2)}$$

$$\text{average deviation} = \Sigma|Xi - Xave|/N \quad \text{Eq. (3)}$$

$$\text{coefficient of variation} = (\text{standard deviation})/(\text{average}) \quad \text{Eq. (4)}$$

In the above equations, Xi represents the luminance of the i-th pixel, Xave represents the luminance average of all the pixels of an inspection region, N represents the number of pixels in the inspection region, and Σ represents a sum of the right side terms for all the pixels of the inspection region.

In this embodiment, predetermined fixed values are used as the determination threshold by luminance average and the determination threshold by luminance variance, but it is not limited. In consideration of the state of capturing image and interlot variation the determination thresholds may be corrected as appropriate.

For example, it is also allowable that with respect to a plurality of light-emitting devices captured in a one-screen image by the image capturing unit 2, a luminance average of all the light-emitting devices is first calculated and then the determination threshold is corrected depending on the average degree of the luminance average.

As a result, the quality determination can be performed more properly by correcting light quantity variations of the light source 21 of the image capturing unit 2 over time and luminance deviations among inspection-object lots.

For this purpose, luminance averages are empirically determined previously for samples of a multiplicity (e.g., several hundreds to thousands) of light-emitting devices, and further an average of luminance average of all samples is calculated and stored in storage means as a standard luminance average (reference luminance average) of light-emitting devices. Also, a luminance-average determination threshold and a luminance-variance determination threshold for properly inspecting the inspection object W comprised of a group of light-emitting devices that emit light at the standard luminance average level are previously determined as reference values (luminance-average reference determination threshold and luminance-variance reference determination threshold).

Then, in the inspection of the inspection object W, first, an average among luminance averages of light-emitting devices (inspection-object luminance average) captured in a one-screen image by the image capturing unit 2 is calculated. In this case, a value resulting from multiplying a luminance-average reference determination threshold by a ratio of the inspection-object luminance average to a reference luminance average is used as the luminance-average determination threshold of the inspection object W as shown in Equation (5). Also for luminance variance, as in the case of the luminance average, a luminance-variance determination threshold is corrected depending on the value of the inspection-object luminance average as shown in Equation (6).

$$\text{luminance-average determination threshold} = (\text{luminance-average reference determination threshold}) \times (\text{inspection-object luminance average})/(\text{reference luminance average}) \quad \text{Eq. (5)}$$

$$\text{luminance-variance determination threshold} = (\text{luminance-variance reference determination threshold}) \times (\text{inspection-object luminance average})/(\text{reference luminance average}) \quad \text{Eq. (6)}$$

Also, the correction method for determination thresholds is not limited to correcting the determination threshold proportionally to the magnitude of the inspection-object luminance average, and the determination threshold may also be corrected so as to be nonlinear to the magnitude of the inspection-object luminance average. Furthermore, the determination threshold may be corrected by adding or subtracting an offset value in accordance with the value of an inspection-object luminance average to or from the reference determination threshold.

Instead of the correction of a determination threshold described above, the luminance average and the luminance variance for each light-emitting device of the inspection object W may be corrected. For example, a correction method for the luminance average and the luminance variance corresponding to the examples shown in Equations (5) and (6) is that the luminance average and the luminance variance are multiplied by a correction factor obtained by dividing 'reference luminance average' by 'inspection-object luminance average.' Then, the quality of the light-emitting device is determined in comparison to the determination threshold which is a fixed value. As a result, a correction effect equivalent to the determination threshold correction method can be obtained.

The color determination means 35 receives inputs of inspection region images from the inspection region extracting means 31 on the light-emitting device basis, and extracts a color component indicating a photoluminescence intensity of light of the second wavelength in the inputted inspection region image. Then, the color determination means 35 determines whether or not the inspection region image contains a pixel in which a pixel value of the extracted color component is larger than a color determination threshold (first threshold), which is a predetermined determination threshold. In the case where such a pixel is detected, the color determination means 35 determines the relevant light-emitting device as a defective device.

In the case where such a pixel is not detected, the light-emitting device is determined as an acceptable device. The color determination means 35 outputs a determination result to the total determination means 36.

In this connection, the terms "color component indicating a photoluminescence intensity of light of the second wavelength," refer to a color component having sensitivity to the second wavelength and moreover having low sensitivity to the first wavelength. In a case where a plurality of color components having such a level of sensitivity to the second wavelength that pixels which release light of the relevant wavelength can be inspected are involved, it is preferable to extract the color component having the lowest sensitivity to the second wavelength. With this arrangement, it can detect the light of the second wavelength at high accuracy without being affected by the light of the first wavelength. For example, when the image capturing means 22 performs color separation into the R, G, B three colors while the light of the second wavelength is blue light, the color determination means 35 extracts the B component.

In addition, the extraction method for color components is not limited to selecting one color from color components resulting from the color separation by the image capturing means 22. For example, it is also allowable to calculate and use such components as hue, color differences, chromaticness and the like from color-separated data.

The quality determination by the color determination means 35 may be performed so that when even one pixel having a pixel value of the color component larger than a color predetermined determination threshold is detected within the inspection region, the light-emitting device is determined as a defective device. But, it is also possible that when a predetermined number which is two or more or a number equal to or larger than a number of pixels corresponding to a predetermined area ratio of the inspection region of relevant pixels are detected, the light-emitting device is determined as a defective device. As a result of this, misdetections due to influences of noise or the like can be suppressed.

Also, in a case where one or more relevant pixels as described above are detected, the light-emitting device is determined as a defective device. In such a case, a highest value of pixels in the inspection region is detected and which is larger than the color determination threshold, the light-emitting device is determined as defective. With this arrangement, a determination can be performed equivalent to that obtained by comparing individual pixel values with the color determination threshold.

The total determination means 36 receives inputs of determination results on the light-emitting device basis from the luminance average determination means 33, the luminance variance determination means 34 and the color determination means 35, respectively, so as to totally determine the quality of the relevant light-emitting device from those determination results. The total determination means 36 in this embodiment determines the light-emitting device as acceptable when none of the determination results is a defective device, and determines the light-emitting device as defective when at least one of the determination results is a defective device. The total determination means 36 stores the determination results in the determination result storage means 37 corresponding to the light-emitting devices.

The determination result storage means 37 stores determination results obtained by the total determination means 36 in association with light-emitting devices. Determination results stored in the determination result storage means 37 are used for, for example, screening manufactured light-emitting devices.

In this embodiment, the total determination means 36 is so designed as to make a total determination by using determination results obtained by the luminance average determination means 33, the luminance variance determination means 34 and the color determination means 35 and to store total determination results in the determination result storage means 37, but it is not limited. For example, determination results derived from the luminance average determination means 33, determination results derived from the luminance variance determination means 34, and determination results derived from the color determination means 35 may be stored in the determination result storage means 37 in association with light-emitting devices, instead of total determination results or in addition to total determination results. Also, in the case that screening light-emitting devices is performed immediately after the determination by using determination results, the screening light-emitting devices may be performed by using those determination results without storing the determination results in the determination result storage means 37.

It is also allowable that determination by the luminance average determination means 33, determination by the luminance variance determination means 34 and determination by the color determination means 35 are executed one by one and, in response to each of the three determination results, defective devices are excluded one by one. As a result of this, when a determination as defective made in any one of the three determination results, the light-emitting device can be excluded. That is, without performing the total determination, a screening equivalent to the screening of light-emitting devices based on the total determination result can be achieved. Also, in the case where the three determinations are performed one by one, when a first determination result is a defective device, another determination later done may be omitted because the relevant light-emitting device results is also a defective device even when the total determination is performed.

The analysis unit 3 can be carried out configuring hardware circuits. The analysis unit 3 can also be carried out inspection programs by which a computer containing such hardware resources as a CPU (Central Processing Unit) and storage means (e.g., memory, hard disk) is operated cooperatively as the respective means described above. These programs may be distributed via communication lines or distributed after they are written in recording mediums such as optical disc or magnetic disc and flash memory.

(Inspection Region and Non-Inspection Region)

Next, inspection region and non-inspection region in a light-emitting device will be explained with reference to FIGS. 4A, 4B and 4C.

The inspection object W in this embodiment is provided in a wafer state in which light-emitting devices 10 are two-dimensionally arrayed. Therefore, a plurality of light-emitting devices 10 are shown in a captured image of photoluminescence as shown in FIG. 4A. In this embodiment, the image of photoluminescence is divided into individual light-emitting device 10, and moreover pixels of a predetermined inspection region are extracted from a divisional image of one light-emitting device 10.

(Dividing Light-Emitting Device Region)

Figure 4A:
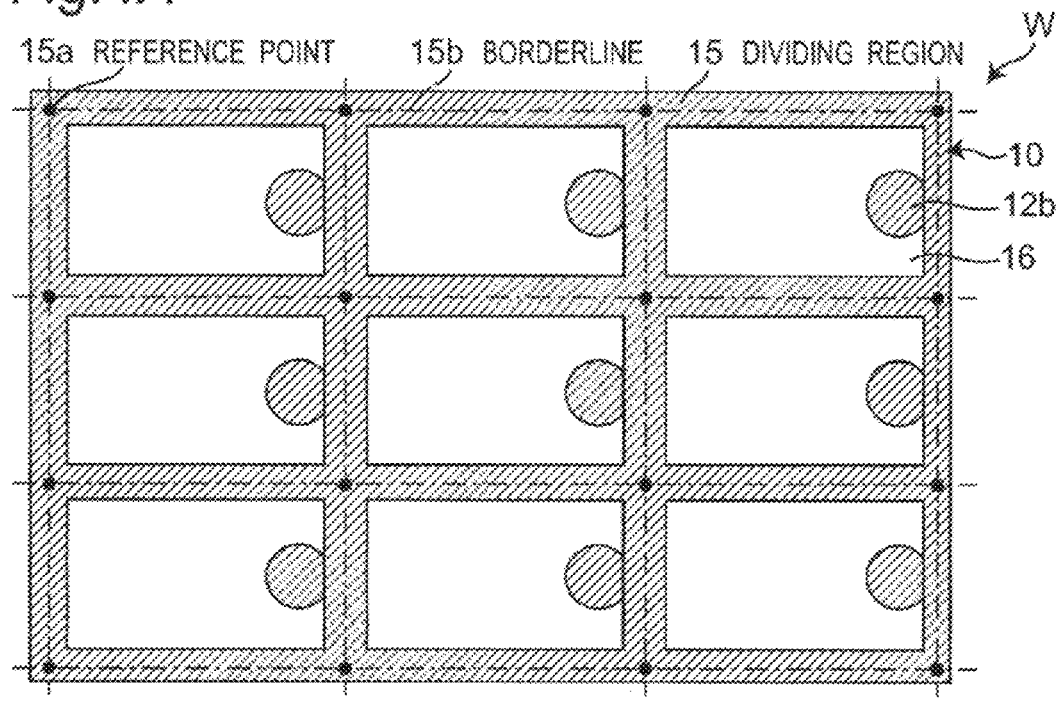
FIG. 4A is a schematic bottom view showing a structure of an inspection object in the inspection method for a semiconductor light-emitting device according to the first embodiment of the invention.

In the wafer-state inspection object W, as shown in FIG. 4A, a plurality of light-emitting devices 10 are two-dimensionally arrayed on one growth substrate. The individual light-emitting devices 10 are divided longitudinally and laterally by dividing regions 15. The dividing regions 15, from which semiconductor layers are eliminated, become non-emitting regions structurally. In the wafer, light-emitting devices 10 are regularly placed in predetermined shape and arrangement. Then, in the image of photoluminescence, the dividing regions 15 are observed as dark longitudinal-and-lateral grid lines as shown by hatching in FIG. 4A, so that light-emitting regions 16 of the light-emitting devices 10 appear to be partitioned by the grid lines. Thus, for example, with centers of the grid lines taken as borderlines 15b, the image of photoluminescence can be divided into image regions of the individual light-emitting devices 10.

In addition, in FIG. 4A, circular-shaped regions hatched on the right-edge side of the light-emitting region 16 are regions for forming an n-side electrode and regions corresponding to recess portion 12b of the semiconductor layers from which the active layer is eliminated. The structure of the light-emitting devices 10 will be described later.

(Extraction of Inspection Region)

In this embodiment, only regions that structurally become light-emitting regions are taken as inspection regions and targeted for calculation of the above-described luminance average and luminance variance. Therefore, pixels that structurally become non-emitting region is extracted as non-inspection region and excluded from the images of the individual light-emitting devices 10 so that only pixels of light-emitting region are extracted as inspection region.

With the division that one region partitioned by the borderlines 15b is regarded as an image region for one light-emitting device 10 as described above, since the light-emitting devices 10 are regularly arrayed, structures of the same configuration are placed at the same positions in the image of any one light emitting device 10, for example with a left-upper intersecting point of the borderlines 15b taken as a reference point 15a.

Figure 4B:
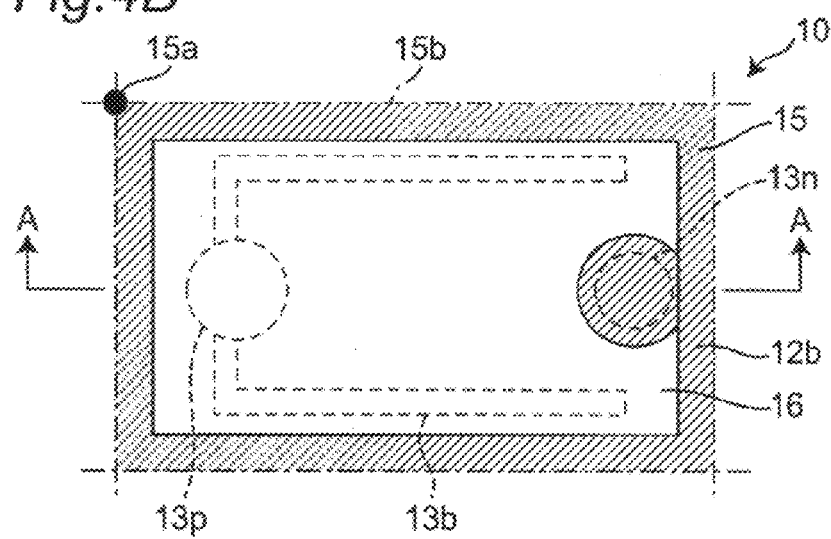
FIG. 4B is a partial enlarged view of FIG. 4A.

Referring to FIG. 4B, which shows an image of photoluminescence of one light-emitting device 10, with the reference point 15a taken as a reference, the light-emitting region 16, the dividing region 15 and the recess portion 12b as non-emitting regions (hatched regions) can be previously determined in correspondence to the structure of the light-emitting device 10. In this embodiment, with the reference point 15a taken as a reference, inspection-region information, which is map information for discriminating whether each pixel within the divisional image of one light-emitting device 10 corresponds to an inspection region or a non-inspection region, is previously prepared and stored in the inspection-region information storage means 32 (see FIG. 1). Then, this inspection-region information is referenced by the inspection region extracting means 31 (see FIG. 1), so that only pixels of inspection regions are extracted.

Figure 4C:
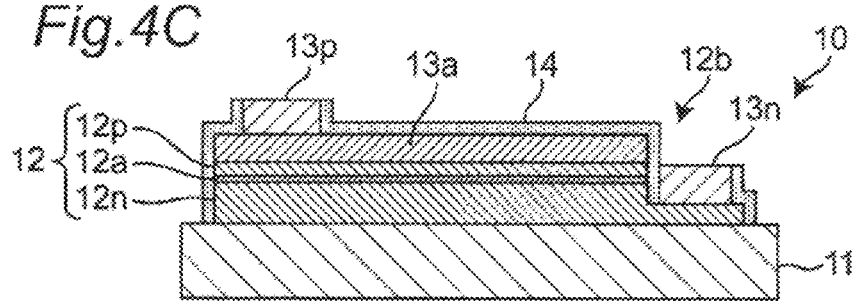
FIG. 4C is a sectional view taken along the line A-A of FIG. 4B.

Referring now to FIG. 4C, the relationship between the light-emitting regions 16, which are inspection regions, as well as the non-emitting regions, which are non-inspection regions, and the structure of the light-emitting devices 10 is explained below. The structure of the light-emitting devices 10 described in this case is only an example and not intended to limit the structure of the light-emitting devices 10, which are the object of the inspection.

For example, the size of one light-emitting device 10 as in a plan view is about 500 μm×300 μm. Also, the size may be either larger one or smaller one. Also, its plan-view shape is not limited to rectangular ones, and light-emitting devices 10 of any appropriate shape such as circular, elliptical and polygonal shapes are applicable. Furthermore, number and shape of the non-emitting regions are also not limited.

The light-emitting device 10 shown in FIG. 4C is composed of a light-pervious growth substrate 11, a semiconductor multilayered body 12 having an n-type semiconductor layer 12n, an active layer 12a and a p-type semiconductor layer 12p multilayered therein, a p-side electrode 13p and an n-side electrode 13n which are positive and negative pad electrodes, respectively, a reflective diffusion electrode 13a for diffusing an electric current from the p-side electrode 13p to the almost all surface of the p-type semiconductor layer 12p, and a light-pervious protective film 14. The semiconductor multilayered body 12 has a recess portion 12b formed at a right-end portion where the entire p-type semiconductor layer 12p and the entire active layer 12a and part of the n-type semiconductor layer 12n have been removed from the top surface to the downward direction. The n-side electrode 13n is provided at the bottom of the recess portion 12b so as to be in electrical contact with the n-type semiconductor layer 12n. Also, the p-side electrode 13p is provided so as to be in electrical contact with the p-type semiconductor layer 12p via the diffusion electrode 13a. In the dividing regions 15, which are outer-edge regions of the light-emitting devices 10, the semiconductor multilayered body 12 is removed.

In addition, the n-side electrode 13n, the p-side electrode 13p and the diffusion electrode 13a are formed of metal layers as an example, being assumed as light-impervious.

In this example, the diffusion electrode 13a is a reflecting electrode, and this light-emitting device 10 is a face-down mounting type device having a light-extracting surface on its growth substrate 11 side. Therefore, image of the photoluminescence is captured from the growth substrate 11 side. In this case, the recess portion 12b is a non-emitting region because it has no active layer 12a. As viewed from the growth substrate 11 side, the recess portion 12b and the dividing region 15 become non-emitting regions while the rest of the region is the light-emitting region, i.e., inspection region.

In addition, when the diffusion electrode 13a is a light-pervious electrode and the light-emitting device 10 is a face-up mounting type device, the image of photoluminescence may be captured from the side on which the semiconductor multilayered body 12 is provided. In this case, as shown by broken line in FIG. 4B, a region shielded from light by the p-side electrode 13p is added to the non-inspection region as a non-emitting region in addition to the dividing region 15 and the recess portion 12b, which are original non-emitting regions. Further, when a extensive portion 13b formed of a metal layer is provided to improve the current diffusivity from the p-side electrode 13p to the diffusion electrode 13a, the region where the extensive portion 13b shown by broken line in FIG. 4B is provided is also added to the non-inspection region.

Even in the case of the face-up mounting type device, when the image is captured from the light-pervious growth substrate 11 side, neither the p-side electrode 13p nor the stretched portion 13b makes a shield from photoluminescence, making it unnecessary to add these regions to non-inspection regions.

As shown above, the inspection regions can be determined depending on the structure of the light-emitting device 10 and the direction of image capturing.

In addition, in order that all the regions having the active layer 12a are inspected for the presence of any light-emitting defective region, it is preferable to capture the image in a direction in which there are no such shielding matters as the p-side electrode 13p or the extensive portion 13b as described above.

(Operations of Inspection Apparatus)

Next, operations of the inspection apparatus 1 will be explained with reference to FIG. 5 (reference to FIG. 1 as required).

Figure 5:
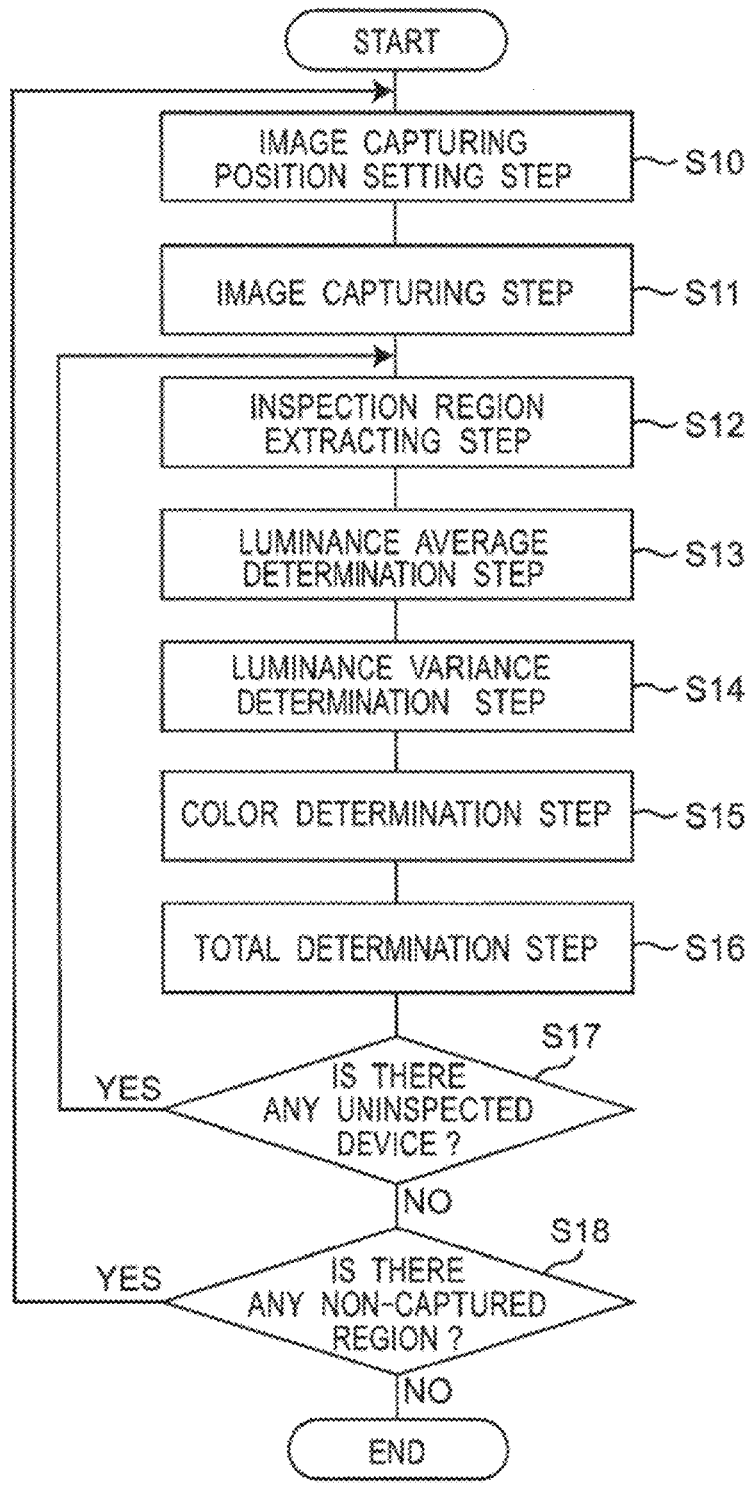
FIG. 5 is a flowchart showing the flow of the inspection method for a semiconductor light-emitting device according to the first embodiment of the invention.

In this embodiment, as shown in FIG. 5, the inspection apparatus 1 performs an image capturing position setting step S10, an image capturing step S11, an inspection region extracting step S12, a luminance average determination step S13, a luminance variance determination step S14, a color determination step S15 and a total determination step S16 for all the regions of the wafer, which is the inspection object W, on the light-emitting device 10 basis.

First, at the image-capturing position setting step S10, as the inspection object W is mounted on the mount 25 of the image capturing unit 2, the inspection apparatus 1 drives the mount 25, which is an XY stage, so as to set an image-capturing position in the inspection object W.

Next, at the image capturing step (image input step) S11, the inspection apparatus 1 captures an image of photoluminescence of the inspection object W by the image capturing unit 2. More specifically, the inspection apparatus 1 turns on the irradiating light source 21 to irradiate the inspection object W with irradiation light via the dichroic mirror 23 and the objective lens 24 for exciting the inspection object W. As a result of this, photoluminescence is released from the inspection object W excited by the irradiating light, and the released photoluminescence is inputted to the image capturing means via the objective lens 24 and further through the dichroic mirror 23. Then, the inspection apparatus 1 generates photoluminescence image data, which is obtained by separating incident photoluminescence into a plurality of color components and converting the individual color components into photoluminescence-intensity signals on the pixel basis, respectively, by the image capturing means 22.

Next, at the inspection region extracting step S12, the inspection apparatus 1 divides the captured image of photoluminescence at step S11 into images on the one light-emitting device 10 basis by the inspection region extracting means 31. On this occasion, the inspection apparatus 1 extracts image data of pixels in the inspection region from the divided image by referencing the inspection-region information stored in the inspection-region information storage means 32.

Next, at the luminance average determination step (photoluminescence-intensity average determination step) S13, the inspection apparatus 1 calculates, by the luminance average determination means 33, a luminance average, which is an average of pixel values indicating luminances, as to image data of the inspection region extracted at step S12. Then, the inspection apparatus 1 compares, by the luminance average determination means 33, the calculated luminance average with a predetermined determination threshold (second threshold) for use in determination based on luminance averages. On this occasion, the light-emitting device is determined as acceptable when the luminance average is equal to or larger than the determination threshold. In a case of the light-emitting device is determined as defective when the luminance average is smaller than the determination threshold.

Next, at the luminance variance determination step (photoluminescence-intensity variation determination step) S14, the inspection apparatus 1 calculates, by the luminance variance determination means 34, a luminance variance, which is a variance of pixel values indicating luminances, as to image data of the inspection region extracted at step S12. Then, the inspection apparatus 1 compares, by the luminance variance determination means 34, the calculated luminance variance with a predetermined determination threshold (third threshold) for use in determination based on luminance variances. On this occasion, the light-emitting device is determined as acceptable when the luminance variance is equal to or smaller than the determination threshold and the light emitting device is determined as defective when the luminance variance is larger than the determination threshold.

Next, at the color determination step S15, the inspection apparatus 1 extracts, by the color determination means 35, a color component indicating a photoluminescence intensity of light of the second wavelength from image data of the inspection region extracted at step S12. Then, the inspection apparatus 1 compares, by the color determination means 35, a pixel value of the extracted color component with a predetermined determination threshold (first threshold) for use in determination based on color with each other for all the pixels in the inspection region. On this occasion the light-emitting device is determined as defective when a pixel having a pixel value of the color component larger than the determination threshold is detected, or determined as acceptable when such a pixel is not detected.

All of the process of step S13, the process of step S14 or the process of S15 may be performed first. Moreover the three processes may be performed in parallel.

Next, the inspection apparatus 1 references, by the total determination means 36, the result determined at step S13, the result determined at step S14, and the result determined at step S15, where the light-emitting device 10 is determined as defective when at least one of the three results is a determination as a defective device (step S16). The result of this total determination is stored in the determination result storage means 37 in association with the inspection-object light-emitting device 10.

Next, the inspection apparatus 1 checks, by the analysis unit 3, whether or not there remains any image of uninspected light-emitting devices 10 in the image of photoluminescence captured at step S11 (step S17). When there remains any image of uninspected light-emitting devices 10

(Yes at step S17), the processing flow returns to step S12, followed by analysis of an image of the next uninspected light-emitting device 10.

Meanwhile, when there remains no uninspected light-emitting device 10 (No at step S17), the inspection apparatus 1 checks, by the analysis unit 3, whether or not there remains any non-captured region of the inspection object W (step S18). In the case that there remains any non-captured region (Yes at step S18), the processing flow returns to step S10, where an image-capturing position is set for the image capturing of the next region by the image capturing unit 2.

On the other hand, when there remains no non-captured region (No at step S18), the inspection apparatus 1 finishes the processing.

In this embodiment, a quality determination is made based on images of photoluminescence obtained by capturing a plurality of light-emitting devices 10 in a one-screen image in the state that the light-emitting devices 10 are in an integrated state (e.g., wafer state). As a result of this, the inspection time can be shortened as compared with cases where the defective-device determination is made based on emitting spectra of individual semiconductor light-emitting devices.

In this embodiment, the inspection object W, in which a plurality of light-emitting devices 10 are arrayed, is divided into a plurality of regions and captured for images one by one, and images of a plurality of light-emitting devices 10 in dividing regions are separated one by one so as to be inspected. But, it is not limited. For example, it is also possible that the whole inspection object W is captured for an image by one-time image capturing. In this case, the loop determination of step S18 is unnecessary. It is also allowable that one light-emitting device 10 is captured up in one captured image. In this case, the loop determination of step S17 is unnecessary. Furthermore, it is allowable that the inspection object W is a single light-emitting device 10. In this case, the loop determinations of step S17 and step S18 are unnecessary.

Second Embodiment

Manufacturing Method of Semiconductor Light-Emitting Device

Next, as a second embodiment of the invention, a semiconductor light-emitting device manufacturing method including the inspection method according to the first embodiment as an inspection step will be described below with reference to FIG. 6 (also reference to FIGS. 1, 4A, 4B and 4C as required).

In this embodiment, the light-emitting device 10 having structure shown in FIG. 4C is taken as an example of the semiconductor light-emitting device to be manufactured. Also, nitride semiconductor is taken as the semiconductor material in the following description.

As shown in FIG. 6, the semiconductor light-emitting device manufacturing method according to the second embodiment includes a semiconductor light-emitting device formation step S100, an inspection step S101, a singulation step S102, and a screening step S103. These steps are performed in succession.

(Semiconductor Light-Emitting Device Formation Step)

At the semiconductor light-emitting device formation step S100, semiconductor light-emitting devices 10 having structure as shown in FIG. 4C are formed in a wafer state of two-dimensional array.

In more detail, first, a semiconductor multilayered body 12 in which an n-type semiconductor layer 12$n$, an active layer 12$a$ and a p-type semiconductor layer 12$p$ are laminated successively is formed on a growth substrate 11 formed from sapphire or the like.

Specific compositions of the n-type semiconductor layer 12$n$, the active layer 12$a$ and the p-type semiconductor layer 12$p$ are not particularly limited, and materials suitable for semiconductor light-emitting devices such as GaN, GaAs, InGaN, AlInGaP, GaP, SiC and ZnO may be used. In particular, GaN-based compound semiconductors represented by a general formula of $In_xAl_yGa_{1-x-y}N$ ($0 \le X$, $0 \le Y$, $X+Y \le 1$) can preferably be used as nitride semiconductor materials.

All of these semiconductor layers may have single-layer structure, but may also have a multilayer structure which contains layers different in composition, film thickness or the like from one another or in a superlattice structure or the like. In particular, the active layer 12$a$ is preferably provided in a single quantum well structure or multiple quantum well structure formed of multilayered thin films having the quantum effect.

Generally, such semiconductor layers may be made up in a homostructure, heterostructure or double-heterostructure or the like having MIS junction, PIN junction or PN junction. GaN-based compound semiconductor layers can be formed by known techniques such as MOCVD (Metal Organic Chemical Vapor Deposition), HVPE (Hydride Vapor Phase Epitaxy), MBE (Molecular Beam Epitaxy), or other processes. Also, film thicknesses of the semiconductor layers are not particularly limited, and those of various film thicknesses are applicable.

The multilayer structure of the semiconductor layers may be exemplified by a buffer layer made of AlGaN, an undoped GaN layer, an n-side contact layer made of Si-doped n-type GaN, a superlattice layer in which a GaN layer and an InGaN layer are alternately stacked, an active layer of the multiquantum well structure in which a GaN layer and an InGaN layer are alternately stacked, a superlattice layer in which a Mg-doped AlGaN layer and a Mg-doped InGaN layer are alternately stacked, a p-side contact layer made of Mg-doped GaN, and the like.

With the semiconductor multilayered body 12 formed in the way shown above, in a region of part of the top surface of the semiconductor multilayered body 12, a recess portion 12$b$ in which the n-type semiconductor layer 12$n$ is exposed at the bottom surface is formed by removing part of the p-type semiconductor layer 12$p$, the active layer 12$a$ and the n-type semiconductor layer 12$n$ by etching process.

Concurrently with this the semiconductor multilayered body 12 for the dividing regions 15 for partitioning the individual light-emitting devices 10, is also removed by etching process. In addition, with regard to the dividing regions 15 part of the n-type semiconductor layer 12$n$ may be removed as in the recess portion 12$b$, or the entirety of the n-type semiconductor layer 12$n$ may be removed so as to make the growth substrate 11 exposed.

Next, an n-side electrode 13$n$, which is a pad electrode, is formed on the bottom surface of the recess portion 12$b$. Also, in regions that become light-emitting regions where neither the p-type semiconductor layer 12$p$ nor the active layer 12$a$ is removed, a p-side electrode 13$p$, which is a pad electrode, is formed at part of the diffusion electrode 13$a$, as well as its top surface, that covers substantially entire surface of the top surface of the p-type semiconductor layer 12$p$.

Further, on the whole surface of the wafer, an insulative protective film 14 of SiO$_2$ or the like is formed, for example, by sputtering.

By the above-described processes, the semiconductor light-emitting devices 10 in the wafer state are formed.

(Inspection Step)

Next, at the inspection step S101, the quality of the light-emitting property is determined on the basis of each semiconductor light-emitting device 10 formed in the wafer. The quality inspection step S5101 is performed by the inspection method according to the first embodiment described above. Therefore, description of the inspection step S101 is omitted.

In addition, quality determination results which are inspection results, are stored in the determination result storage means 37 in association with the individual semiconductor light-emitting devices 10.

(Singulation Step)

Next, at the singulation step S102, the wafer is divided according to the dividing regions 15 by dicing process, scribing process or the like so as to divide the wafer into chips of the individual semiconductor light-emitting devices 10.

(Screening Step)

Finally, at the screening step S103, with respect to the individualized semiconductor light-emitting devices 10 (chips), semiconductor light-emitting devices 10 other than those not determined as defective as a result of the quality determination of the inspection step S101 are screened as acceptable devices. Thus, chips having defective light-emitting regions and therefore being highly likely to decrease in luminance or fail due to time deterioration can be removed as defective devices as well as defective devices of low luminance average.

Now concrete examples of the singulation step S102 and the screening step S103 are described in detail below. It is noted that steps from a front-surface-side adhesive sheet bonding step to a 'back-surface-side adhesive sheet stretching step' described below correspond to the singulation step S102, and an 'acceptable device extracting step' corresponds to the screening step S103.

(Front-Surface-Side Adhesive Sheet Bonding Step)

After the quality determination as to the individual semiconductor light-emitting devices 10 at the inspection step S101 is finished, an adhesive sheet coated with a UV (Ultraviolet)-curing type adhesive is bonded to the whole top surface (surface on which semiconductor layers are stacked) of the wafer in which semiconductor light-emitting devices 10 are two-dimensionally arrayed. This adhesive sheet is a sheet in which, for example, a resin sheet of polyolefine or the like is coated with an adhesive that is cured and decreased adhesion by UV irradiation.

(Dicing Step)

Next, the wafer is subjected to dicing from the back surface side, i.e. growth substrate 11 side, of the wafer, by which the light-emitting devices 10 are divided.

(Back-Surface-Side Adhesive Sheet Stretching Step)

Next, an adhesive sheet is bonded to the back surface side of each semiconductor light-emitting device 10. The adhesive sheet to be bonded on the back surface side may be one similar to the adhesive sheet bonded on the front surface side, but it is preferable that the adhesive sheet has stretchability and that the adhesive is other than the ultraviolet-curing type.

(Front-Surface-Side Adhesive Sheet Peeling Step)

Next, UV light is applied to the front-surface-side adhesive sheet so that the adhesive is cured so as to decrease the adhesion. Then, the front-surface-side adhesive sheet having decreased the adhesion is peeled off. Thus, it follows that the adhesive sheet is bonded on the back surface side of each semiconductor light-emitting device 10.

(Back-Surface-Side Adhesive Sheet Stretching Step)

Next, the back-surface-side adhesive sheet is stretched in longitudinal-and-lateral array directions of the semiconductor light-emitting devices 10. As a result of this, the semiconductor light-emitting devices 10 singulated in the dicing step can be made apart from one another while keeping their positional relation of two-dimensional array. Thus, the semiconductor light-emitting devices 10 can more easily be captured individually.

(Acceptable-Device Extracting Step)

Next, acceptable semiconductor light-emitting devices are extracted according to the total determination result determined on the semiconductor light-emitting device 10 basis at the inspection step S101. The extraction of semiconductor light-emitting devices 10 may be performed by, for example, attaching a collet having a suction nozzle at its end to an XYZ stage, moving the collet to positions where a semiconductor light-emitting device 10 determined as an acceptable device is placed, one after another, and sucking and picking up the semiconductor light-emitting device 10 from the front surface side of the wafer by the collet. In capturing of a semiconductor light-emitting device 10 by the collet, it is preferable that the semiconductor light-emitting device 10 is pushed up by a pin from the back surface side of the wafer via the adhesive sheet. With this arrangement, the semiconductor light-emitting device 10, which is an object of extraction, can be picked up easily from the adhesive sheet.

Although acceptable devices are picked up in this embodiment, yet it is also allowable that defective devices are picked up and removed. In this case, it follows the semiconductor light-emitting devices 10 that are left after removal of all the defective devices are screened as acceptable.

Although the inspection method for a semiconductor light-emitting device, as well as the semiconductor light-emitting device manufacturing method including the inspection method as a step, according to the present invention have been described specifically by way of embodiments of the invention hereinabove, yet the gist of the invention is not limited to these descriptions and should be widely construed based on the description of appended claims. Also, it is needless to say that changes and modifications of the embodiments in various ways based on those descriptions are included in the gist of the invention.

REFERENCE SIGNS LIST

1 inspection apparatus
2 image capturing unit (image input means)
21 irradiating light source
22 image capturing means
23 dichroic mirror
24 objective lens
25 mount
3 analysis unit
31 inspection region extracting means
32 inspection-region information storage means
33 luminance average determination means (photoluminescence-intensity average determination means)
34 luminance variance determination means (photoluminescence-intensity variation determination means)
35 color determination means 36 total determination means
37 determination result storage means
10 semiconductor light-emitting device (light-emitting device)
11 growth substrate
12 semiconductor multilayered body
12*n* n-type semiconductor layer
12*p* p-type semiconductor layer
12*a* active layer
12*b* recess portion
13*n* n-side electrode
13*p* p-side electrode
13*a* diffusion electrode
13*b* extensive portion
14 protective film
15 dividing region
15*a* reference point
15*b* borderline
16 light-emitting region
W inspection object

The invention claimed is:

1. A method of inspecting a semiconductor light-emitting device having an active layer configured to emit light of a predetermined first wavelength, the method comprising:
   irradiating the semiconductor light-emitting device with light of a wavelength shorter than the first wavelength, using an irradiating light source;
   capturing an image of photoluminescence emitted from the active layer upon the irradiation of the semiconductor light-emitting device, using an image sensor;
   extracting a region of the semiconductor light-emitting device from the captured image, as an inspection region, using a computer; and
   determining presence of a pixel having a pixel value of a color component indicating that a photoluminescence intensity of a second wavelength light of a shorter wavelength than the first wavelength is larger than a predetermined first threshold, using the computer; and
   determining that the semiconductor light-emitting device is defective when said pixel is present in the inspection region.

2. The method according to claim 1, wherein the inspection region is a region other than predetermined non-emitting regions of the semiconductor light-emitting device.

3. The method according to claim 1, further comprising:
   calculating an average value of a photoluminescence intensity over pixels in the inspection region, using the computer; and
   determining that the semiconductor light-emitting device is defective when the average value of the photoluminescence intensity is smaller than a predetermined second threshold, using the computer.

4. The method according to claim 1, further comprising:
   calculating an average value of a photoluminescence intensity over pixels in the inspection region, using the computer; and
   calculating a variation value indicating a degree of variation of the photoluminescence intensity over the pixels in the inspection region, using the computer; and
   determining that the semiconductor light-emitting device is defective upon determining that at least one of (i) the average value of the photoluminescence intensity is smaller than a predetermined first threshold, and (ii) the variation value is larger than a predetermined second threshold, using the computer.

5. The method according to claim 4, wherein the variation value is determined based on any one of variance, standard deviation, average deviation and coefficient of variation of photoluminescence intensity in the inspection region.

6. The method according to claim 1,
   wherein the step of capturing an image of photoluminescence emitted from the active layer comprises capturing an image of a plurality of semiconductor light-emitting devices at once, and
   wherein the step of extracting a region of the semiconductor light-emitting device comprises separately extracting a region of each of the semiconductor light-emitting devices from the extracted image, as an inspection region.

7. The method according to claim 3, wherein the calculation of the average value of the photoluminescence intensity is performed in parallel with the determination of the presence of said pixel in the inspection region.

8. The method according to claim 4, wherein the calculation of the average value of the photoluminescence intensity and the calculation of the variation value are performed in parallel with the determination of the presence of said pixel in the inspection region.

9. The method according to claim 5, wherein the calculation of the average value of the photoluminescence intensity is performed in parallel with the determination of the presence of said pixel in the inspection region.

10. The method according to claim 2, further comprising:
    calculating an average value of a photoluminescence intensity over pixels in the inspection region, using the computer; and
    determining that the semiconductor light-emitting device is defective when the average value of the photoluminescence intensity is smaller than a predetermined second threshold, using the computer.

11. The method according to claim 2, further comprising:
    calculating an average value of a photoluminescence intensity over pixels in the inspection region, using the computer; and
    calculating a variation value indicating a degree of variation of the photoluminescence intensity over the pixels in the inspection region, using the computer; and
    determining that the semiconductor light-emitting device is defective upon determining that at least one of (i) the average value of the photoluminescence intensity is smaller than a predetermined first threshold, and (ii) the variation value is larger than a predetermined second threshold, using the computer.

12. The method according to claim 11, wherein the variation value is determined based on any one of variance, standard deviation, average deviation and coefficient of variation of photoluminescence intensity in the inspection region.

13. The method according to claim 10, wherein the calculation of the average value of the photoluminescence intensity and the calculation of the variation value are performed in parallel with the determination of the presence of said pixel in the inspection region.

14. The method according to claim 4, wherein the calculation of the average value of the photoluminescence intensity and the calculation of the variation value are performed in parallel with the determination of the presence of said pixel in the inspection region.

15. The method according to claim 5, wherein the calculation of the average value of the photoluminescence intensity and the calculation of the variation value are performed in parallel with the determination of the presence of said pixel in the inspection region.

16. A method of manufacturing a semiconductor light-emitting device, the method comprising:
   forming a semiconductor light-emitting device;
   inspecting the semiconductor light-emitting device formed in the step of forming the semiconductor light-emitting step to determine whether or not the semiconductor light-emitting device is defective; and
   determining that the semiconductor light-emitting device is an acceptable device when the semiconductor light-emitting device is not determined as defective in the step of inspecting the semiconductor light-emitting device,
   wherein the step of inspecting the semiconductor light-emitting device is implemented according to the inspection method defined in claim 1.

17. A method of manufacturing a semiconductor light-emitting device, the method comprising:
   forming a semiconductor light-emitting device;
   inspecting the semiconductor light-emitting device formed in the step of forming the semiconductor light-emitting device to determine whether or not the semiconductor light-emitting device is defective; and
   determining that the semiconductor light-emitting device is an acceptable device when the semiconductor light-emitting device is not determined as defective in the step of inspecting the semiconductor light-emitting device,
   wherein the step of inspecting the semiconductor light-emitting device is implemented according to the inspection method defined in claim 2.

18. A method of manufacturing a semiconductor light-emitting device, the method comprising:
   forming a semiconductor light-emitting device;
   inspecting the semiconductor light-emitting device formed in the step of forming the semiconductor light-emitting device to determine whether or not the semiconductor light-emitting device is defective; and
   determining that the semiconductor light-emitting device is an acceptable device when the semiconductor light-emitting device is not determined as defective in the step of inspecting the semiconductor light-emitting device,
   wherein the step of inspecting the semiconductor light-emitting device is implemented according to the inspection method defined in claim 7.

19. A method of manufacturing a semiconductor light-emitting device, the method comprising:
   forming a semiconductor light-emitting device;
   inspecting the semiconductor light-emitting device formed in the step of forming the semiconductor light-emitting device to determine whether or not the semiconductor light-emitting device is defective; and
   determining that the semiconductor light-emitting device is an acceptable device when the semiconductor light-emitting device is not determined as defective in the inspection step of inspecting the semiconductor light-emitting device,
   wherein the step of inspecting the semiconductor light-emitting device is implemented according to the inspection method defined in claim 8.

\* \* \* \* \*